United States Patent [19]

Kruse

[11] Patent Number: 5,379,775
[45] Date of Patent: Jan. 10, 1995

[54] LOW AMPLITUDE PACING ARTIFACT DETECTION APPARATUS AND METHOD USING ISOLATION AMPLIFIER TO MINIMIZE DISTORTION

[75] Inventor: John M. Kruse, Columbia Heights, Minn.

[73] Assignee: Medtronic, Inc., Minneapolis, Minn.

[21] Appl. No.: 138,158

[22] Filed: Oct. 15, 1993

[51] Int. Cl.6 .......................... A61B 5/0402
[52] U.S. Cl. .................. 128/697; 128/908; 607/27
[58] Field of Search .......... 128/696, 697, 710, 903, 128/904, 908; 607/27, 28

[56] References Cited

U.S. PATENT DOCUMENTS 4,742,831  5/1988  Silvian .................. 128/908
5,307,817  5/1994  Guggenbuhl et al. ............ 128/908

Primary Examiner—George Manuel
Attorney, Agent, or Firm—Harold R. Patton

[57] ABSTRACT

A pacing artifact detection apparatus and method uses a high bandwidth isolation amplifier having low harmonic distortion, high linearity, wide dynamic range, low current leakage, dc coupling, bipolar and high voltage isolation characteristics in conjunction with a high frequency operational amplifier to drive biopotential signals across an isolation barrier at high frequencies with no distortion. The speed of transmission across the isolation barrier is sufficiently high to allow diagnostics and analysis on the pacing artifact being transmitted across the isolation barrier without adversely impacting the reliability of the pacing artifact detection.

6 Claims, 3 Drawing Sheets

INPUT SURFACE ECG  SEE FIG. 3B

ENLARGED PACING ARTIFACT

LOW AMPLITUDE PACING ARTIFACT DETECTION APPARATUS AND METHOD USING ISOLATION AMPLIFIER TO MINIMIZE DISTORTION

BACKGROUND OF THE INVENTION

1. Field of the Invention

This invention relates generally to the field of medical monitoring devices, and more particularly relates to medical devices used to detect low amplitude artifacts produced by artificial cardiac pacing.

2. Description of the Prior Art

A wide variety of cardiac pacemakers are known and commercially available. Pacemakers are generally characterized by which chambers of the heart they are capable of sensing, the chambers to which they deliver pacing stimuli, and their responses, if any, to sensed intrinsic electrical cardiac activity. Some pacemakers deliver pacing stimuli at fixed, regular intervals without regard to naturally occurring cardiac activity. More commonly, however, pacemakers sense electrical cardiac activity in one or both of the chambers of the heart, and inhibit or trigger delivery of pacing stimuli to the heart based on the occurrence and recognition of sensed intrinsic electrical events. A so-called "SSI" pacemaker, for example, senses electrical cardiac activity in a chamber, atrium (A) or ventricle (V), of the patient's heart, and delivers pacing stimuli to the same chamber only in the absence of electrical signals indicative of natural chamber contractions. A "DDD" pacemaker, on the other hand, senses electrical signals in both the atrium and ventricle of the patient's heart, and delivers atrial pacing stimuli in the absence of signals indicative of natural atrial contractions, and ventricular pacing stimuli in the absence of signals indicative of natural ventricular contractions. The delivery of each pacing stimulus by a DDD pacemaker is synchronized with prior sensed or paced events.

Pacemakers are also known which respond to other types of physiological based signals, such as signals from sensors for measuring the pressure inside the patient's ventricle or measuring the level of the patient's physical activity. These devices are labeled "SSIR" for a single chamber version or "DDDR" for a dual chamber version.

As pacemaker technology as well as integrated circuit and lead technologies have evolved, chronic pacing thresholds have approached very low values (<<1.0 volts) and very efficient low current CMOS amplifier designs have become available. What is needed, but still missing in the art of pacing artifact detection however, is an isolation amplifier capable of driving biopotential signals across an isolation barrier at high frequencies above 200 kHz with little or no distortion, substantially higher than frequencies approaching about 70 kHz presently available in the art of pacing artifact detection. Such an amplifier will allow use of software correlators on the pacing artifact which has heretofore been unknown in the art of pacing artifact detection.

SUMMARY OF THE INVENTION

The present invention overcomes the disadvantages of the prior art systems by providing a method of and apparatus for driving high frequency, large or small bipolar amplitude biopotential signals across an isolation barrier with minimal distortion, thereby enhancing detection of a pacing artifact in a patient having artificially paced myocardial contractions. Reliable detection of the pacing artifact is extremely important in monitoring and programming implantable pacemakers. It is necessary to accurately determine whether and when a pacing pulse has occurred and the width of the pulse.

The inventive pacing artifact circuit is programmable. An algorithm is utilized to detect the noise level and the pacing artifact amplitude and perform diagnostics and analysis on the artifact. In one embodiment the inventive apparatus includes an isolation amplifier having a high bandwidth of 200 kHz, low harmonic distortion, high linearity of 0.01%, wide dynamic range (20 volts being typical), low current leakage, dc coupling, and high voltage isolation greater than 4000 volts. Combining the isolation amplifier discussed above with an operational amplifier capable of driving the biopotential signals at high frequencies and large amplitudes provides the present inventive apparatus allowing diagnostics and analysis as discussed hereinbefore on a pacing artifact. The wide dynamic range also discussed hereinbefore provides a signal to noise ratio corresponding to 14 bits of precision. Manufacturability, cost, and reliability are greatly enhanced over the available apparatus based on prior art technology since the inventive apparatus requires no potentiometers for adjusting DC offsets for example, as these offsets can now be eliminated using software in real time at frequencies of 200 kHz and above when used with a digital signal processor.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENT

Figure 1:
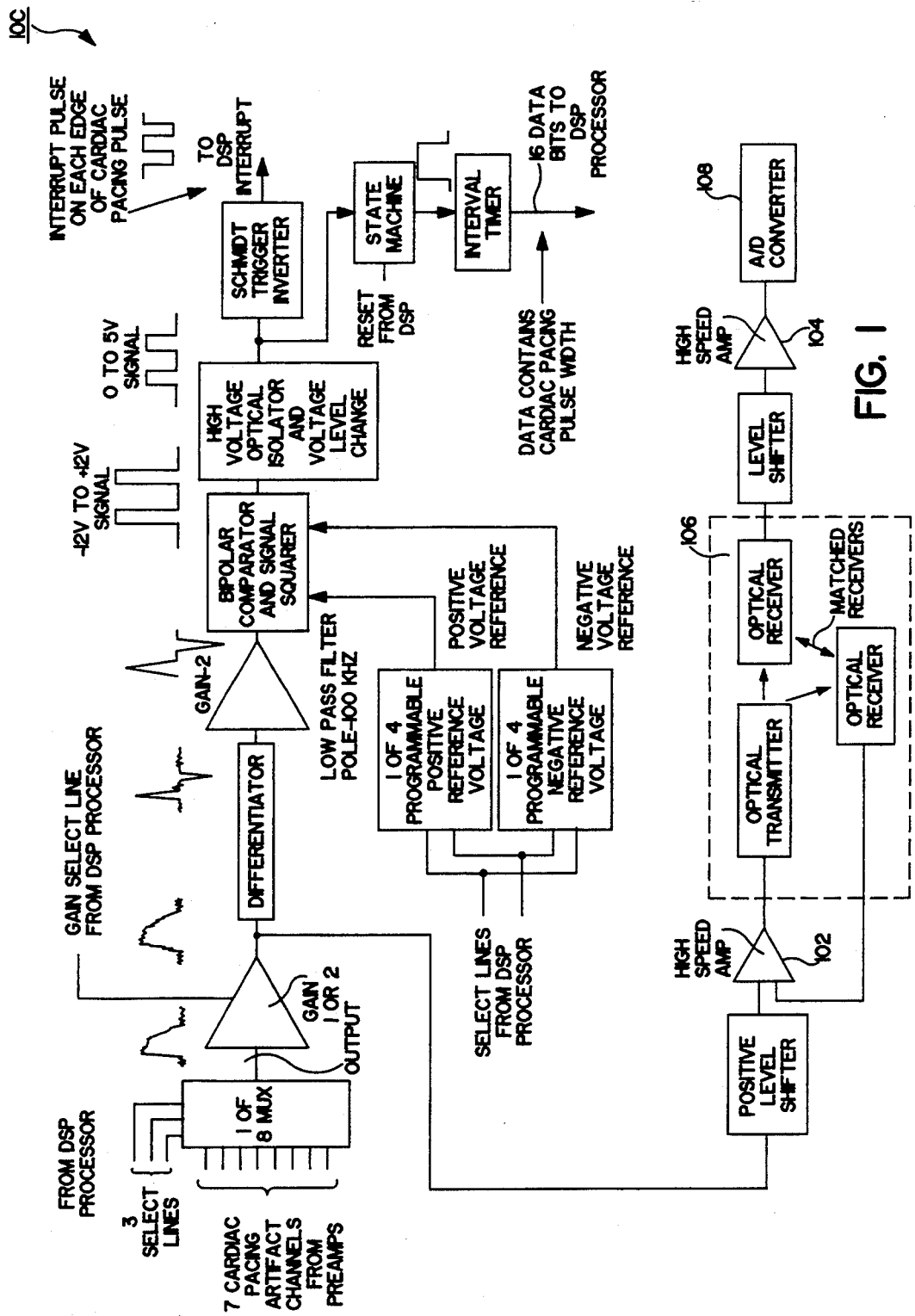
FIG. 1 illustrates a block diagram of a heart pacing pulse detection apparatus using the inventive isolation circuit.
Figure 2:
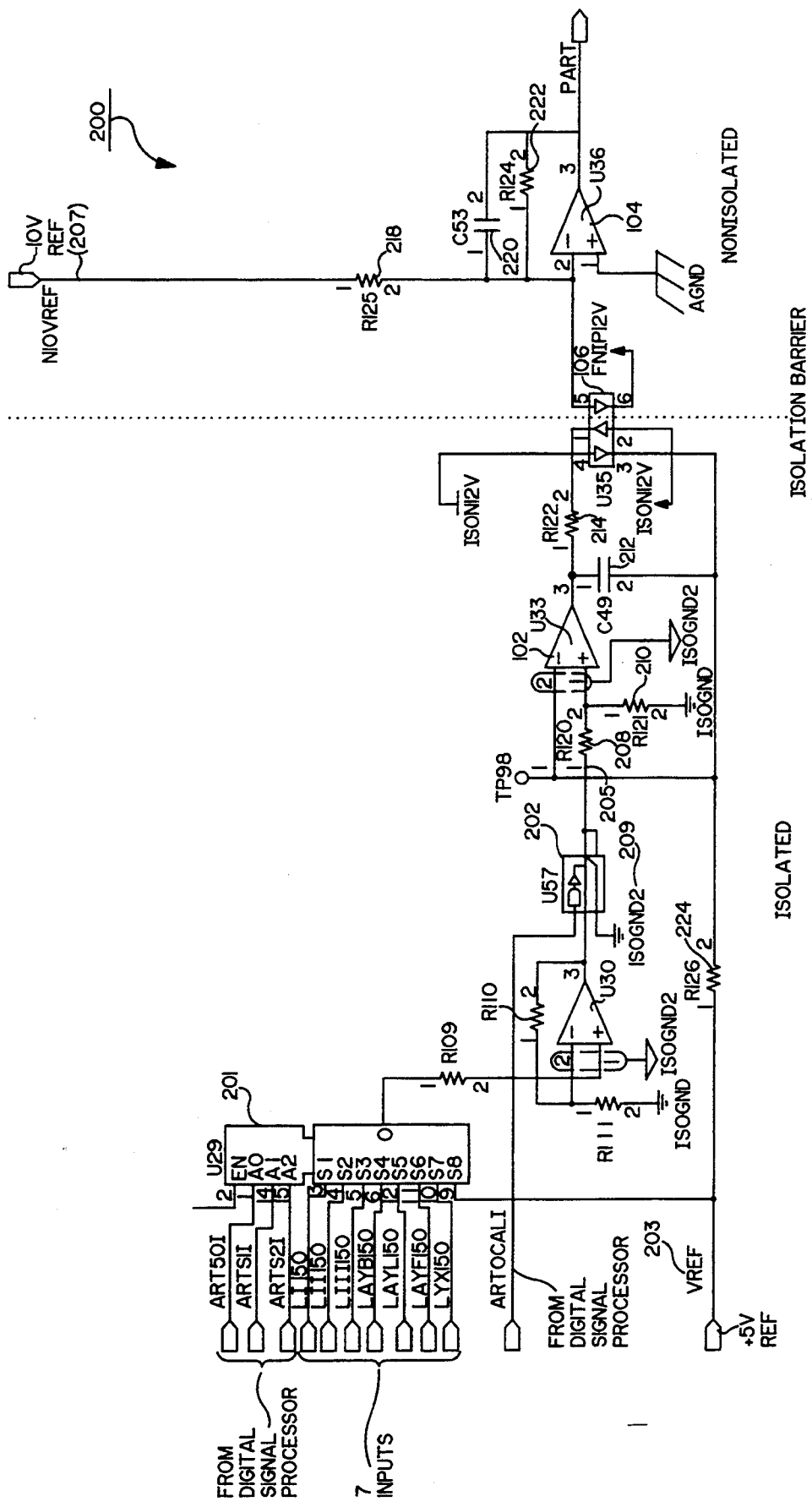
FIG. 2 is a schematic diagram illustrating one embodiment of the present inventive isolation circuit for transmitting biopotential signals across an isolation barrier at high frequencies with no distortion.

Looking now at FIG. 1, a block diagram of a heart pacing pulse detection apparatus 100 using one embodiment of the present inventive isolation system is illustrated. A more detailed embodiment of the present inventive isolation system depicted in FIG. 1 is illustrated in FIG. 2 and will be used hereinafter to describe how the inventive system operates. Element 201 is an analog 8 to 1 multiplexer that allows any one of 7 signals to be selected and outputed by using 3 select lines from a digital signal processor. An eighth signal 203 is a 5 volt reference signal used for calibrating the linear optical isolator 200.

Element 202 is an analog switch that can switch in a 0 volt reference signal also used for calibrating the linear optical isolator 200.

Elements 206, 208, 210, 212, 214, 216, 218, 220, 222, and 224 comprise the inventive linear optical isolator 200.

The signal at pin 1 (205) of resistor R120 (208), assuming +/−12v power, can be +/−10 volts. Resistors R120 (208) and R121 (210) divide the signal at pin 1 (205) by 2 and resistor R126 (224) coupled with a +5 volt reference 203 and Op Amp U33 (102) level shift the selected input signal to +5 volts. The signal is then driven across the isolation barrier 106 at high frequency via optical isolator 106. Resistor R122 (214) is used as a current limit. One receiving diode within optical isolator 106 is used as feedback into Op Amp U33 (102) to linearize the system 200. Capacitor C49 (212) is used to stabilize the system 200 as the system 200 is inherently unstable at high frequency due to the delay in optical transmission through optical isolator 106.

Resistor R125 (218) coupled with a negative 10 volt reference 207 and Op Amp U36 (104) level shifts the signal to be centered around 0 volts. Capacitor C53 (220) coupled with resistor R124 (222) creates a pole to stabilize Op Amp U36 (104). The output of Op Amp U36 (104) is fed into a high speed analog to digital converter (A/D) 108 shown in FIG. 1.

Figure 4:
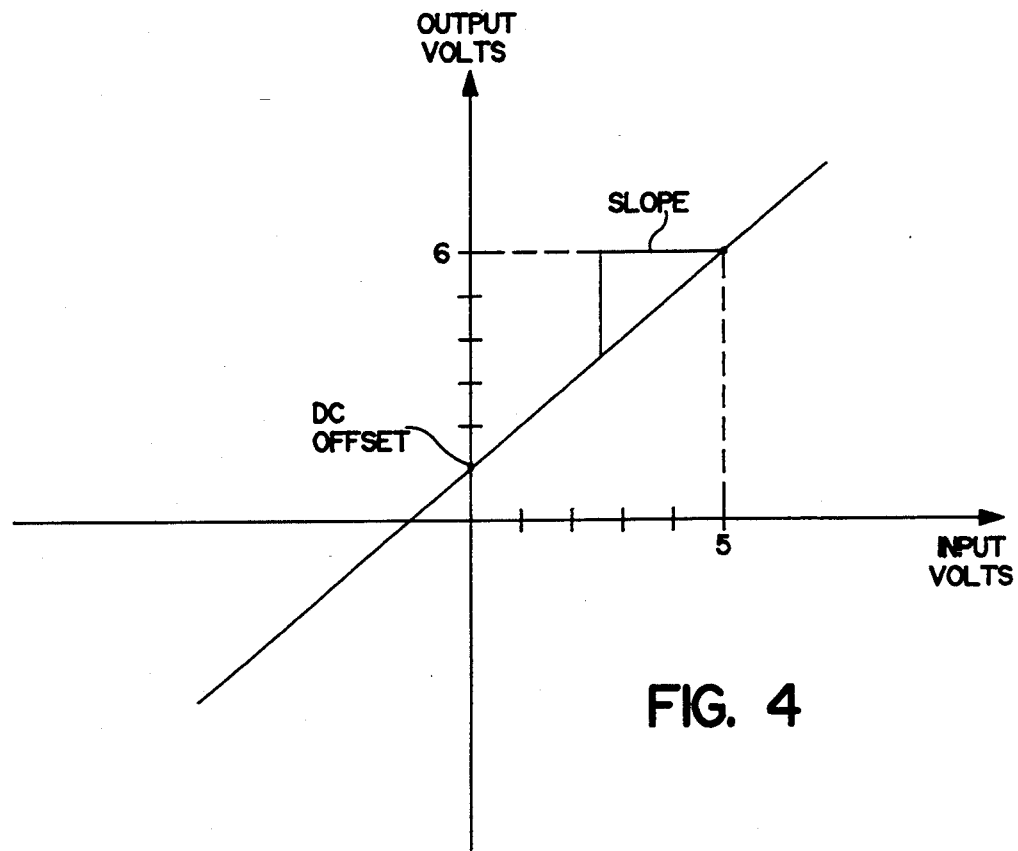
FIG. 4 is a graphical illustration of gain and DC offset correction factors for the isolation circuit shown in FIG. 2.

Because the gains from the transmitting diode to the two receiving diodes within optical isolator 106 are not matched exactly, a gain and offset error is created. In addition, other errors caused by normal tolerances of the system 200 Op Amps 102, 104 and resistors 208,210, 214, 218,222 and 224 also add to the gain and offset error. To remove this error, a digital signal processor (DSP), not shown, outputs a command and selects the +5 volt reference signal 203 available at the input to multiplexer 201. The analog to digital converter (A/D) 108 converts this signal and the DSP stores this value. The DSP then outputs another command and selects the 0 volt reference signal 209. The A/D 108 converts this signal and the DSP stores this value. The correct gain (determined by a slope value dependent on the two calibrated input values stored in the DSP) for the system 200 as well as the DC offset (determined by a y-intercept value dependent on the two calibrated input values stored in the DSP) for system 200 can now be calculated and stored. For the sake of clarity, a graphical representation of these two input values as discussed hereinbefore is illustrated in FIG. 4.

Each analog to digital conversion can be corrected in real time by adjusting the gain and the DC offset of each input signal. This is possible in the present inventive system 200 because of the single cycle mathematical capabilities of the digital signal processor (not shown). A significant advantage offered with this correction scheme is the elimination of the need for costly potentiometers, heretofore required by other pacing artifact detection systems known in the art.

Figure 3A:
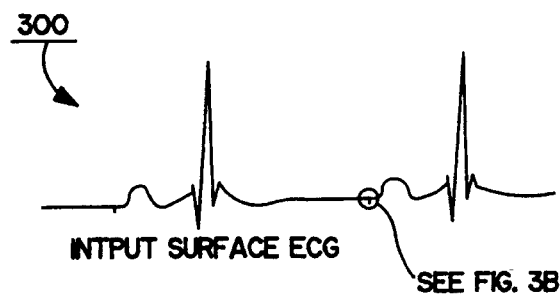
FIG. 3 illustrates an impact surface ECG and an enlarged pacing artifact.
Figure 3B:
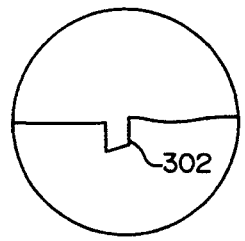

Moving on to FIG. 3, there is illustrated an enlarged representative view of a pacing artifact 302 and a patient's skin surface ECG signal 300 containing the artifact 302. It is this artifact 302 which the present inventive system 200 detects with high levels of accuracy at frequencies up to and above 200 kHz, and which heretofore has been only successfully measured at frequencies up to approximately 70 kHz.

From the foregoing detailed descriptions of particular embodiments of the present invention, it should be apparent that a pacemaker pacing artifact detection apparatus has been disclosed which is provided with the capability of detecting pacing artifact signals at lower amplitudes hereto before available in the art of pacing artifact detection. Furthermore, the inventive apparatus rejects and cancels out common mode noise signals generated by multiple noise sources beyond frequencies of 200 kHz, a feature also not hereto before available in the art of pacing artifact detection.

While the invention has been described above in connection with a particular embodiment, one skilled in the art will appreciate that the invention is not necessarily so limited. It will thus be understood that numerous other embodiments, examples, uses, modifications of, and departures from the teachings disclosed may be made, without departing from the spirit and scope of the present invention as claimed herein.

I claim:

1. An apparatus for driving pacing artifact signals across an electrical isolation barrier, said barrier having an isolated side and a nonisolated side, and wherein said artifact signals are transmitted across said isolation barrier at frequencies up to and above 200 kHz with no distortion, said apparatus comprising:
    (a) sensing means coupled to said isolated side of said isolation barrier for sensing said pacing artifact signals on said isolated side of said isolation barrier;
    (b) high frequency amplifying means coupled to said isolated side of said isolation barrier and further coupled to said sensing means for amplifying said sensed pacing artifact signals at said frequencies up to and above 200 kHz; and
    (c) high frequency isolating means coupled to said high frequency amplifying means for transferring said amplified pacing artifact signals on said isolated side of said isolation barrier to said nonisolated side of said isolation barrier at said frequencies up to and above 200 kHz.

2. The apparatus of claim 1 further comprising high frequency amplifying means for amplifying said pacing artifact signal on said nonisolated side of said isolation barrier at said frequencies up to and above 200 kHz.

3. The apparatus of claim 1 wherein said coupling between said high frequency isolating means and said high frequency amplifying means is a direct coupling.

4. A method of driving pacing artifact signals across an electrical isolation barrier having an isolated side and a nonisolated side, said signals being sensed on said isolated side and driven from said isolated side to said nonisolated side at frequencies up to and above 200 kHz with no measurable distortion, said method comprising the steps of:
    (a) sensing said pacing artifact signals on said isolated side of said isolation barrier;
    (b) amplifying said sensed pacing artifact signals at said frequencies up to and above 200 kHz; and
    (c) driving said amplified pacing artifact signals on said isolated side of said isolation barrier to said nonisolated side of said isolation barrier with an isolation amplifier at said frequencies up to and above 200 kHz.

5. The method of claim 4 further comprising the step of directly coupling said amplified pacing artifact signals on said isolated side of said isolation barrier to said isolation amplifier.

6. The method of claim 4 further comprising the step of amplifying said pacing artifact signal on said nonisolated side of said isolation barrier.

* * * * *